US012691064B2

(12) United States Patent
Underwood et al.

(10) Patent No.: US 12,691,064 B2
(45) Date of Patent: Jul. 28, 2026

(54) INHALABLE THERAPEUTIC AGENT

(71) Applicant: Cila Therapeutics Inc., Jamaica Plain, MA (US)

(72) Inventors: Dennis Underwood, Jamaica Plain, MA (US); Ashfaq Mahmood, Jamaica Plain, MA (US); Safia K. Rizvi, Jamaica Plain, MA (US)

(73) Assignee: Cila Therapeutics Inc., Jamaica Plain (MA)

( * ) Notice: Subject to any disclaimer, the term of this patent is extended or adjusted under 35 U.S.C. 154(b) by 705 days.

(21) Appl. No.: 17/433,220

(22) PCT Filed: Feb. 21, 2020

(86) PCT No.: PCT/US2020/019317
§ 371 (c)(1),
(2) Date: Aug. 23, 2021

(87) PCT Pub. No.: WO2020/172594
PCT Pub. Date: Aug. 27, 2020

(65) Prior Publication Data

US 2022/0117893 A1 Apr. 21, 2022

Related U.S. Application Data

(60) Provisional application No. 62/809,316, filed on Feb. 22, 2019.

(51) Int. Cl.
*A61K 9/127* (2025.01)
*A61K 9/00* (2006.01)
*A61K 45/06* (2006.01)

(52) U.S. Cl.
CPC ............ *A61K 9/127* (2013.01); *A61K 9/0073* (2013.01); *A61K 45/06* (2013.01)

(58) Field of Classification Search
CPC .............................. A61K 9/0073; A61P 11/12
See application file for complete search history.

(56) References Cited

U.S. PATENT DOCUMENTS

2008/0279784 A1* 11/2008 Cartt ...................... A61P 25/22 514/219

FOREIGN PATENT DOCUMENTS

WO WO-2008063341 A2 * 5/2008 .......... A61K 31/496
WO WO-2017/123315 A2 7/2017

OTHER PUBLICATIONS

Ourique, A. F. et al., Redispersible liposomal-N-acetylcysteine powder for pulmonary administration: development, in vitro characterization and antioxidant activity, Sep. 28, 2014, European Journal of Pharamecutical Sciences, vol. 65, 174-182 (Year: 2014).*

Darquenne, C., Aerosol deposition in health and disease, 2012, Journal of Aerosol Medicine and Pulmonary Drug Delivery, vol. 25, 140-147 (Year: 2012).*

Illing, E. A. et al., Management of the upper airway in cystic fibrosis, 2014, Current Opinion in Pulmonary Medicine, vol. 20, 623-631 (Year: 2014).*

Label: Acetylcysteine solution, Sep. 24, 2012, DailyMed, https://dailymed.nlm.nih.gov/dailymed/lookup.cfm?setid=8fd7b5d8-f6b1-4d0a-9ec6-446c5f89762a, accessed Jun. 14, 20204 (Year: 2012).*

Steen S. N. et al., Evaluation of a new mucolytic drug, 1974, Clinical Pharmacology and Therapeutics, vol. 16, 58-62 (Year: 1974).*

Elborn, J.S. et al., Safety and efficacy of prolonged levofloxacin inhalation solution treatment for cystic fibrosis and chronic Pseudomonas aeruginosa airway infection, Feb. 28, 2016, Journal of Cystic Fibrosis, vol. 15, 634-640 (Year: 2016).*

Elphick, H.E. et al., Antifungal therapies for allergic bronchopulmonary aspergillosis in people with cystic fibrosis, Cochrane Database of Systematic Reviews, 2016, Issue 11, CD002204, 10 pages (Year: 2016).*

Shah, S.P. et al., Development of liposomal Amphotericin B dry powder inhaler formulation, Drug Delivery, 2004, vol. 11, 247-253 (Year: 2004).*

Cipolla, D. et al., Development of liposomal ciprofloxacin to treat lung infections, Pharmaceutics, 2016, vol. 8 (Year: 2016).*

Extended European Search Report for European Patent Application No. 20758770.0, dated Oct. 31, 2022 (9 pages).

Misra et al., "Recent advances in liposomal dry powder formulations: preparation and evaluation," Expert Opin Drug Deliv. 6(1):71-89 (Jan. 2009).

* cited by examiner

*Primary Examiner* — Bethany P Barham
*Assistant Examiner* — Paul Hoerner
(74) *Attorney, Agent, or Firm* — Wiggin and Dana LLP

(57) ABSTRACT

A therapeutic agent for treating airways of a subject comprising one or more types or sizes of particles, each particle comprising in turn a biodegradable enclosure containing a mucolytic or another drug therein. A dispersing apparatus may be used to deliver metered doses of mucolytic and may be configured for self-administration by the subject. Encapsulation of the mucolytic in a liposomal formulation may prevent premature oxidation and maintain drug efficacy upon delivery to a target location in upper or lower respiratory tract.

13 Claims, No Drawings

INHALABLE THERAPEUTIC AGENT

CROSS-REFERENCE DATA

The present patent application claims a priority date benefit from a Provisional U.S. Patent Application No. 62/809,316 filed 22 Feb. 2019, entitled "Specific Inhaled Formulations of Small and Large Molecules as Therapeutic Agents" by the same inventors, which is incorporated herein by reference in its entirety.

BACKGROUND

Without limiting the scope of the invention, its background is described in connection with inhalable therapeutic agents. More particularly, the invention describes inhalable particles comprising a mucolytic contained within a biodegradable encapsulation such as a liposomal formulation for the treatment of lung, airways and respiratory diseases.

The main function of the respiratory system is to draw air into the lungs of a subject and allow the exchange of gases with blood circulating and perfusing the lung tissues. The lungs are the body's most important respiratory organ where normal gaseous exchange of essential oxygen and carbon dioxide as well as carbon monoxide are carried out effectively and efficiently. The lungs preform its gaseous exchange function as it has direct access and exposure to the outside air and environment, with which this gaseous exchange is carried out. To achieve this essential role the epithelial lung tissues are kept moist with a thin film of hydrated mucus, which include various proteins, including mucin, physiological cations and anions such as sodium, potassium, calcium, chloride, bicarbonate, carbonates, phosphate etc., that are maintained in aqueous osmolar concentrations, in addition to other proteins and enzymes.

The mucus transport system is the fundamental defense of the airways against inhaled debris, bacteria and other infectious agents. Inhaled foreign particles are trapped in the mucus layer and subsequently propelled out of the lungs via mucuciliary clearance. The well hydrated mucus facilitates this ciliary clearance of these foreign agents and keeps the respiratory tract protected. Mucociliary clearance (MCC) in healthy and normal lungs is facilitated by the movement of cilia, that clear well hydrated mucus/liquid, and is also facilitated by cellular ion transport system, such as the sodium and chloride transport system. In the absence of sufficient mucus hydration and functioning cilia and ion transport systems, the mucus becomes excessively viscous and adherent forming "mucus plugs". This results in the airways obstruction, inability to breath properly (insufficient oxygen exchange) and recurrent lungs airways and ear infections. Recurrent infection causes permanent lung damage and could lead to respiratory failure.

The initial cause of the various respiratory diseases may vary and include environmental exposure to various compounds, free radicals, reactive oxygen species (ROS), and others (due to smoking, toxin exposure, chronic respiratory infection etc.), as well as genetic etiologies such as mutation in functional proteins in Cystic Fibrosis (CF) and Primary Ciliary Dyskinesia (PCD). In the various respiratory and lung diseases, it is widely established that a common manifestation of a disease is a lack of, or diminished, normal mucus clearance and formation of thick, viscous and adhesive mucus or sputum. Increasingly highly viscous and adherent mucus or sputum is considered to be caused by an increase of chronic "oxidative stress", lack of hydration and movement of mucus and results in an altered state of mucus, a common element of which is oligomerization of normal mucus proteins such as mucin and other proteins via multiple inter- and intra-molecular disulfide bond formation. This is coupled with an increased non-covalent protein-protein interaction that further aggregates the protein(s) structures due to increased hydrogen-bonding and hydrophobic inter- and intra-protein interactions. These molecular changes/interactions thereby increase the elasticity and viscosity of the naturally maintained mucus and result in a decreasing efficiency of the natural mucus clearance mechanisms and system. The mucus clearance is also hampered by dysfunction in Cilia (tiny hair like structure that line the respiratory apparatus) and ion transport proteins caused by genetic mutations in relevant proteins. Collectively, the resulting inter- and intra-protein disulfide bonds and various hydrogen bonding, protein-protein hydrophilic and hydrophobic interactions are responsible altering the normal mucus structure and building and sustaining the protein oligomerization resulting in mesh-like protein network commonly known as "mucus plugs". Furthermore, inflammatory processes, including recruitment of neutrophils to the site of inflammation, toxic exposure or infection result in an increased oxidative environment with concomitant cell death, this in turn accumulates cellular debris including DNA, lipids, fibrin and foreign particles and pathogen leading to thick mucus that is too viscous and adhesive like for normal flow and removal. The decreased MCC, which in turn serve to exacerbate the mucus plugs and provide a fertile growth environment for respiratory bacterial growth. This cascade of molecular processes cumulatively leads to chronic breathing problems, recurrent airway, lung and nasal infections with persistence and progression toward lung damage.

Altered structured and highly viscous mucus plug are key manifestation of multiple pulmonary disease such as Primary Ciliary disease (PCD), Cystic Fibrosis, Bronchiectasis, sinusitis, Rhinosinusitis, and Chronic Obstructive Pulmonary Disease (COPD, an umbrella term used for a broad array for pulmonary disorders such as Emphysema, Bronchitis etc.). Aggregated-structured mucus or sputum has altered macromolecular composition and biophysical properties that vary with disease. The underlying cause of these diseases vary based on genetic and environmental factors, but common features in all these diseases are diminished mucus clearance, resulting in airway obstruction, entrapment of bacteria and pathogen, recurrent infection and repeated inflammation. This in turn, progressively damages the lungs and can eventually cause respiratory failure or/and need for lung transplant.

Current standard of care for most of these diseases (with the exception of CF in certain population) remains focused on addressing symptoms and complications. These comprise:

Prevent, control and treat infections of the lungs sinus and ear, (oral and IV antibiotics and anti-infectives)

Hydrate and remove the trapped viscous mucus and sputum. (moisture inhalers and saline bronchial lavage)

Reduce swelling and Inflammation (corticosteroids and bronchodilators)

Expand airways to facilitate breathing (bronchodilators)

CPT (Chest Physical therapy) manually or with the assistance of devices.

Surgery (Tympanostomy, sinus surgery, lung transplant)

All of these methods with the exception of surgery show only marginal or temporary relief and do not effectively address the basic problem of thick, viscous, adhesive mucus plugs that are the main culprit, causing breathing difficulties and trapped cellular, particulate debris and pathogens, recurrent infections and irreversible and progressive lung damage.

A safe, effective and dependable therapeutic option such as the composition described in this invention for disrupting the critical bonds responsible for polymerization of protein/the formation of mucus plugs and thus fluidification of viscous mucus is therefore much needed to address and alleviate the basic issue in many rare and common lung and respiratory/pulmonary diseases and facilitate MCC. This would significantly improve the quality of life for patients with the above-mentioned disease. It would first, fluidify mucus and clear the airways obstruction, improve gaseous exchange and address breathing problems, Second, prevent recurring infection by completely exposing pathogen (previously shielded in mucus plugs) to antibiotics, thus rendering other intervention more effective and, third, prevent permanent lung damage.

There is also a need to protect a mucolytic from oxidation while being delivered to the treatment site. Certain mucolytic agents can readily oxidize before reaching their target, which may diminish their efficacy. This may explain inconsistent results in clinical trials. The need exists to provide protection from oxidation for a mucolytic in order to maximize its potency.

SUMMARY

Accordingly, it is an object of the present invention to overcome these and other drawbacks of the prior art by providing novel inhalable therapeutic agents that allow effective dissolution of mucus.

It is another object of the present invention to provide novel inhalable therapeutic agents designed to provide effective treatment at lower doses of the drug so as to reduce possible side effects and allow for administration in repeated applications performed multiple times.

It is a further object of the present invention to provide novel inhalable therapeutic agents configured for administration either by a medical professional or self-administration so as to make such treatment suitable for delivery at home.

It is yet another object of the present invention to provide novel therapeutic agents configures to protect the active drug from oxidation and loss of mucolytic activity prior to its direct delivery at the target site of the airways, whereby preserving its potency until its immediate interaction at the target site.

In the most basic form, the present invention may be described as at least one or several pluralities of inhalable particles. Each particle may comprise a mucolytic or another suitable active therapeutic agent contained within one or several types of biodegradable encapsulations. The number and respective concentration of therapeutic agents including at least one mucolytic, the type of biodegradable encapsulation selected for each therapeutic agent, and the size of inhalable particles may be adjusted depending on a particular type of airways disorder in order to deliver the intended medication to an intended location of the airways to effectively treat the underlying condition.

In embodiments, at least two types and/or sizes of inhalable particles may be enclosed in a single dispersing apparatus configured for self-administration by the subject in repeated applications based on a predetermined schedule. At least one of such inhalable particles may include a mucolytic within a biodegradable encapsulation, such as a liposomal formulation, microsphere, nanoparticles or engineered spray particles.

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

The present invention is aimed to directly address the underlying pathology of a respiratory disease i.e. mucus plugs, decreased mucociliary clearance and its subsequent consequences with inhalable particles comprising a biodegradable enclosure containing pharmaceutical compositions of the compounds consisting of amino acid derivatives, natural and synthetic peptides, small-molecules, vitamins, and/or proteolytic and DNA cleaving enzymes as identified below. These molecules may be designed and chosen to cleave disulfide and other bonds, increase the local antioxidant concentration/potential, break and disrupt the hydrogen bonds and hydrophobic interaction in aggregated and altered mucus proteins as well as nucleic acid and lipids. Furthermore, the inhaled biodegradable particles may optionally be tailored to contain drugs, molecular entities or other agents—alone or in various combinations of two or more of these functional agents encapsulated within the same enclosure or in separate enclosures of the same or different sizes. These separately formulated enclosures containing different drugs/agents can optionally be administered together or sequentially and at different times to enhance their individual effectiveness in the treatment.

The invention encompasses therapeutic agents and methods for their direct pulmonary administration through any one or more of the routes including the nasal, intratracheal, and bronchial instillation. The particles of the invention may be delivered by means of administering inhalable liposomes, microspheres, nanoparticles directly to lungs and the respiratory tract. Furthermore, the inhalable particles of the invention may be deployed by direct instillation, inhalation, nebulized-inhalation, aerosolized inhalation or via a nebulized, or aerosolized or inhaled airways route. The methods for this direct delivery by inhalation or the intranasal route envision the use of a dispersing apparatus such as an aerosolized metered dose inhaler, a handheld portable nebulizer or compressor-nebulizer inhaling device capable of delivering the drug encapsulated particles via the inhaled and/or intranasal route. Furthermore, the particles of the therapeutic agent of the present invention may be stored in a dry powder form (such as for a metered inhaler) or in a liquid form (such as for a nebulizer).

In embodiments, a dispersing apparatus may include a device comprising a compressed/pressurized inhalable aerosol delivery device and optionally equipped with a smart digital measurement capability for monitoring of patient compliance. Such a device may include, such as, but not limited to, pulsating membrane nebulizers, vibrating mesh nebulizers, small volume nebulizers, pressured-metered dose inhalers, dry powder inhalers and similar devices capable of inhaled delivery of dry powder containing the particles of the invention or liquid solutions containing these particles. Such dispersing devices may have one or more separated medicine holding chambers containing the inhaled particles as described below and configured for simultaneous or sequential administration of such particles according to a predetermined schedule.

For the purposes of this description, the terms "enclosure", "encapsulation", "liposome", "formulation", and "coating" are used interchangeably to describe a biodegradable particle containing a suitable drug for treatment of airways. The term "biodegradable" is used herein to describe a biocompatible material which breaks down upon contact with the tissues of the airways and releases the drug inside thereof. Release of the active drug from within these enclosures may be an immediate release, a controlled-release, a sustained-release, and/or a time-released process. In addition, various particles may be combined together for a time-release of desired drugs on a predetermined spaced apart schedule.

In embodiments, exemplary liposome delivery vehicles may include closed vesicular, colloidal, bilayer structures formed by lipid, phospholipid, sphingolipids, glycolipids, long chain fatty acids and biologically acceptable surfactants that form liposomes of varying sizes and compositions. While the specific composition may be an inhaled liposomal formulation, encapsulating these molecules, compounds, agents and/or enzymes may serve to create a physiologically compatible drug-delivery vehicle for these drugs/agents.

The inhaled liposomal formulation(s) may be uniquely tailored for and administered directly to the target location of a respiratory site of pathology, thereby avoiding systemic drug exposure caused when said drugs or agents are administered intravenously, intraarterially, intramuscularly or in oral formulations. This in turn may allow for a significant reduction of the dosage of these agents, which in turn may alleviate many of the side effects associated therewith.

Liposomes and nanoparticles represent unique drug carriers that can site-specifically deliver the drug while protecting it from interaction with environment (blood, metabolism, exposure to air, etc.). As such these vehicles are suitable for protecting the mucolytic or another drug of choice from premature oxidation, thereby preserving its potency until the drug is released at the target site. Inherent to the structure/formulation of the liposome are certain phospholipids, surfactants and other aqueous excipient molecules. When delivered to the targeted site, these components may further serve to liquefy the mucus by disrupting hydrophobic interactions within and between these proteins, as well as penetrate the mucus thru lipids.

The main functional drug to be contained within a biodegradable encapsulation is a mucolytic. Broadly speaking, such mucolytic may include amino-acid derivatives, peptides, peptide analogues and/or small-molecules as active agents, alone or in combination of one or more of the agents. In embodiments, such mucolytic may be selected from the following compounds:

N-Acetylcysteine in concentrations from about 5% to about 25%, such as 5%, 10%, 15%, 20%, 25% or any concentration in between as the invention is not limited in this regard;

2-Mercaptoethane Sulfonate in concentrations from about 5% to about 25%, such as 5%, 10%, 15%, 20%, 25% or any concentration in between as the invention is not limited in this regard;

L-α-Ureido-mercaptopropionic Acid in concentrations from about 50 mg/ml to about 250 mg/ml, such as 50 mg/ml, 100 mg/ml, 150 mg/ml, 200 mg/ml, 250 mg/ml or any other concentration within this range as the invention is not limited in this regard;

Bromhexine;

Ascorbic acid, such as Vitamin-C (reduced Ascorbic acid or an ascorbate salt thereof);

N-Butylcysteine;

Reduced Glutathione, such as natural tri-peptide Glutathione in the reduced form of Glutathione;

N-derivatives and C-derivatives of amino acid Cysteine;

Di-peptide of Cysteine and Glutamic acid;

Di-peptide of Aspartic acid;

Ambroxol Hydrochloride;

DNAse, such as a recombinant DNAse; and

DNA cleaving agent.

In embodiments, an active agent may include amino-acid derivatives that are chosen from D and/or L-isomer derivatives according to the formula:

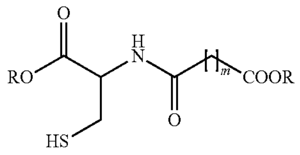

m = 1-3
R = H, Ethyl, alkyl for example:

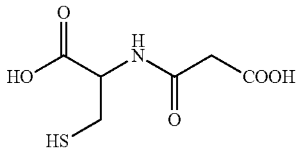

m = 1, R = H
3-((1-carboxy-2-mercaptoethyl)amino)-3-oxopropanoic acid

In further embodiments of the invention, the mucolytic may be an amino-acid derivative such as D- and/or L-isomer of the amino acid derivative according to the formula:

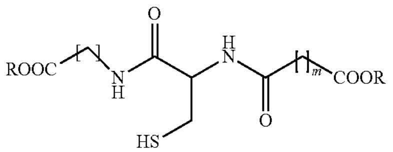

n = 1-3
m = 1-3
R = H, Et, alkyl for example:

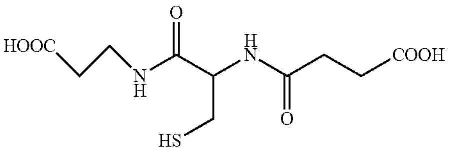

n = 2; R = H; m = 2
3-((1-((2-carboxyethyl)amino)-3-mercapto-1-oxopropan-2-yl)amino)-3-oxopropanoic acid In further embodiments of the invention, the mucolytic may be a peptide or peptide analogue such as D- and/or L-isomer of amino-acids according to the formula:

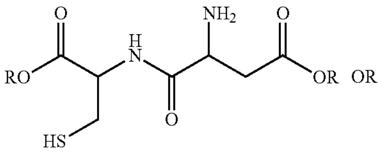

Cys-Asp-1
R = H, Ethyl or alkyl

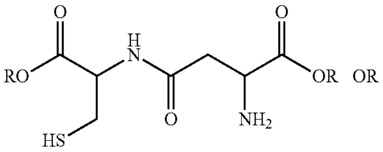

Cys-Asp-2
R = H, Ethyl or alkyl

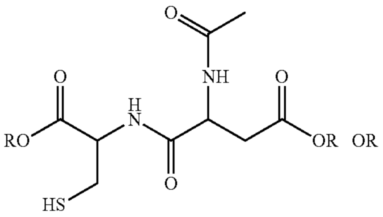

Cys-(N-acetyl-Asp)-1
R = H, Ethyl or alkyl

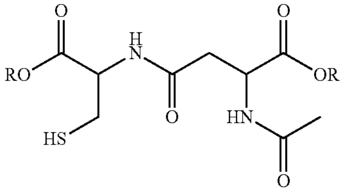

Cys-(N-acetyl-Asp)-2
R = H, Ethyl or alkyl

In yet further embodiments of the invention, the mucolytic may be a peptide or a peptide analogue such as D- and/or L-isomer of the amino acids in the peptides according to the formula:

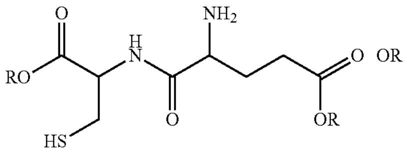

Cys-Glu-1
R = H, Ethyl or alkyl

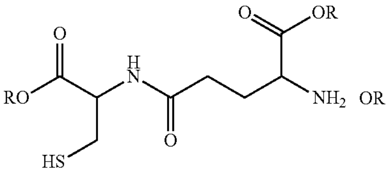

Cys-Glu-2
R = H, Ethyl or alkyl

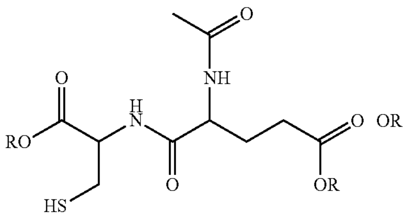

Cys-(N-acetylGlu)-1
R = H, Ethyl or alkyl

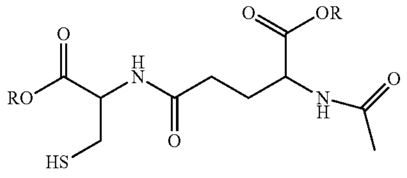

Cys-(N-acetylGlu)-2
R = H, Ethyl or alkyl

In yet other embodiments, the mucolytic may be Vitamin-E or a small-molecule Sodium-2-Mercaptoethane Sulfonate, Tris(2-carboxyethyl)phosphine Hydrochloride.

Since mucus may serve as a form of cover for bacteria, commonly used antibiotics may be unable to reach and attack these bacteria. Breaking the structured mucus and its subsequent liquification may enable an antibiotic to reach the pathogens and bacteria and clear the infection. Therefore, the present invention further includes a simultaneous or sequential administration of inhaled liposomal formulation of a mucolytic as well as an antibiotic, anti-viral, anti-fungal, or another anti-infective compound.

In embodiments, and anti-infective agent may include quinolones (such as Nalidixic Acid, Cinoxacin, Ciprofloxacin and Norfloxacin and the like), Sulfonamides (e.g., Sulfanilamide, Sulfadiazine, Sulfamethoxazole, Sulfisoxazole, Sulfacetamide, and the like), aminoglycosides (e.g., Streptomycin, Gentamicin, Tobramycin, Amikacin, Netilmicin, Kanamycin, and the like), tetracyclines (such as Chlortetracycline, Oxytetracycline, Methacycline, Doxycycline, Minocycline and the like), para-aminobenzoic acid, diaminopyrimidines (such as Trimethoprim, often used in conjunction with Sulfamethoxazole, pyrazinamide, and the like), penicillins (such as Penicillin G, Penicillin V, Ampicillin, Amoxicillin, Bacampicillin, Carbenicillin, Carbenicillin indanyl, Ticarcillin, Azlocillin, Mezlocillin, Piperacillin, and the like), penicillinase resistant penicillin (such as Methicillin, Oxacillin, Cloxacillin, Dicloxacillin, Nafcillin and the like), first generation cephalosporins (such as Cefadroxil, Cephalexin, Cephradine, Cephalothin, Cephapirin, Cefazolin, and the like), second generation cephalosporins (such as Cefaclor, Cefamandole, Cefonicid, Cefoxitin, Cefotetan, Cefuroxime, Aefuroxime axetil, Cefinetazole, Cefprozil, Loracarbef, Ceforanide, and the like), third generation cephalosporins (such as Cefepime, CefoperaZone, Cefotaxime, Ceftizoxime, Ceftriaxone, Ceftazidime, Cefixime, Cefpodoxime, Ceftibuten, and the like), other beta-lactams (such as Imipenem, Meropenem, Aztreonam, Clavulanic acid, Sulbactam, Tazobactam, and the like), beta-lactamase inhibitors (such as Clavulanic acid), Chloramphenicol, macrollides (such as Erythromycin, Azithromycin, Clarithromycin, and the like), Lincomycin, Clindamycin, Spectinomycin, Polymyxin B, polymixins (such as Polymyxin A, B, C or D, $E_1$. Colistin A), or $E_2$, Colistin B or C, and the like) colistin, Vancomycin, Bacitracin, Isoniazid, Rifampin, Ethambutol, Ethionamide, Aminosalicylic Acid, Cycloserine, Capreomycin, Sulfones (such as Dapsone, Sulfoxone Sodium, and the like), Clofazimine, Thalidomide, or any other antibacterial agent that can be lipid encapsulated. Antiinfectives can include antifungal agents, including polyene antifungals (such as Amphotericin B, Nystatin, Natamycin, and the like), Flucytosine imida (such as Miconazole, Clotrimazole, Econazole, Ketoconazole, and the like), triazoles (such as Itraconazole, Fluconazole, and the like), Griseofulvin, Terconazole, Butoconazole Ciclopirax, CiclopiroX Olamine, Haloprogin, Tolnaftate, Naftifine, Terbinafine, or any other antifungals that can be lipid encapsulated or complexed and pharmaceutically acceptable salts thereof and combinations thereof.

In embodiments, more than one biodegradable particle may be contained together in a single therapeutic agent. For example, the therapeutic agent of the invention may include a combination of first inhalable particles and second inhalable particles in a dispersing apparatus. Each of the first inhalable particles may in turn comprise a first mucolytic contained within a first biodegradable encapsulation, as described above. Each of the second inhalable particles may in turn comprise the same first or a second mucolytic contained within a second biodegradable encapsulation. In other embodiments, the second particle may contain an anti-infective agent or another drug. As a result, the first mucolytic and/or the second mucolytic are protected from oxidation prior to release from these respective first biodegradable encapsulations or the second biodegradable encapsulations and subsequent absorption at a target location of the airways of the subject.

To assure delivery to more than one target location, first particles may be sized differently than second particles. In embodiments, first particles may be sized from about 5 to about 50 microns for predominant delivery to upper respiratory tract. In embodiments, the size of first particles may be 5, 10, 15, 20, 25, 30, 35, 40, 45, 50 microns or any size inbetween as the invention is not limited in this regard.

Second particles may be sized to be from about 0.01 to about 6 microns to assure predominant delivery at the lower respiratory tract. In embodiments, second particles may be sized to be about 0.01, 0.1, 0.2, 0.3, 0.4, 0.5, 0.6, 0.7, 0.8, 0.9, 1, 2, 3, 4, 5, 6 microns or any size in between as the invention is not limited in this regard.

In other embodiments, drug concentration may also vary between first and second particles. Exemplary concentration of the mucolytic for the first particle may be from about 5 mg to about 200 mg, and for the second particle from about 10 mg to about 100 mg.

In further embodiments, more than two particles may be provided and sized to assure predominant deposition of different particles at different locations along the airways upon inhalation of the therapeutic agent by the subject. In embodiments, three, four or more particle sizes may be provided to allow for a more uniform coverage of the desired portion of the airways with the therapeutic agent of the invention.

In addition to liposomal formulations with lipids, other biodegradable materials or surfactants may be used to create a biodegradable enclosure of the invention. This may be done for a purpose of timed release. In one example, first particles may be designed to release the drug immediately upon contact with the target site, while second particles may be designed to release the drug with a predetermined delay. Combining two or more time-release particles with predetermined times of drug release may be used to create a sustained schedule of drug release following a single or limited number of inhalations. This sustained or controlled release formulation would offer convenient dosing for patients.

Particles may differ between each other not only in size but also in the content of the drug. In embodiments, the same mucolytic may be provided in two or more concentrations within biodegradable particles with different time of release designs. In other embodiments, two different mucolytics may be used to form two or more types of particles of the invention. In yet further embodiments, first particles may contain a mucolytic, while second particles may contain an antibiotic or an anti-viral drug.

In embodiments, a total dose of a mucolytic delivered in a single application may vary from about 5 milligrams to about 200 milligrams, such as 5, 10, 20, 30, 40, 50, 75, 100, 125, 150, 175, 200 milligrams and can be delivered using any of the methods and devices described above.

The present invention as described above may be advantageously used to enable enhanced muco-ciliary clearance (MCC) and directed towards alleviating and treating of common fundamental problems and symptoms observed in lung and respiratory airways diseases. A list of conditions and diseases that may benefit from the present invention may include:

Primary Ciliary Dyskinesia (PCD),
Cystic Fibrosis (CF),
Bronchiectasis (BE),
Sinusitis
Rhinosinusitis
Bronchiolitis Obliterans (BO),
Emphysema,
Bronchitis,
Pneumonia,
Pneumonitis,
COPD,
Other lung and airways diseases,
Other muco-obstructive diseases
Viral and bacterial infections of Lungs, Sinus and Ear It is contemplated that any embodiment discussed in this specification can be implemented with respect to any method of the invention, and vice versa. It will be also understood that specific embodiments described herein are shown as a way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A therapeutic agent for treating airways of a subject, said therapeutic agent comprising a combination of first inhalable particles, second inhalable particles, and third inhalable particles, each of said first inhalable particles comprising a first mucolytic contained within a first biodegradable encapsulation, each of said second inhalable particles comprising said first or a second mucolytic contained within a second biodegradable encapsulation and wherein the first biodegradable encapsulation is distinct from the second biodegradable encapsulation, whereby said first mucolytic and/or said second mucolytic are protected from oxidation prior to release from said respective first biodegradable encapsulation or said second biodegradable encapsulation and absorption at a target location of said airways of said subject, and each of said third inhalable particles comprising a lipid encapsulated anti-infective agent.

2. The therapeutic agent as in claim 1, wherein at least one of said first biodegradable encapsulation has a liposomal formulation.

3. The therapeutic agent as in claim 1, wherein said first particles are sized to be from about 5 microns to about 50 microns, said second particles are sized to be from about 0.01 microns to about 6 microns, whereby said first particles are configured for predominant absorption at a first target location of said airways and said second particle are configured for predominant absorption at a second target location of said airways.

4. The therapeutic agent as in claim 3, wherein said first target location of said airways is upper respiratory tract and said second target location of said airways is lower respiratory tract.

5. The therapeutic agent as in claim 3 further comprising additional particles of mucolytics contained within biodegradable encapsulations, said additional particles are sized for predominant absorption at additional locations of said airways upon inhalation of said therapeutic agent by said subject.

6. The therapeutic agent as in claim 1, wherein the first mucolytic is released immediately upon inhalation of said therapeutic agent by said subject, and the second mucolytic is released with a predetermined delay, whereby providing an extended time release mucolytic therapy to said subject.

7. The therapeutic agent as in claim 1, wherein said first inhalable particles and said second inhalable particles are stored in a solution form or a dry powder form or a gel form.

8. The therapeutic agent as in claim 7, wherein the solution form and the gel form are derived from a dry powder form.

9. The therapeutic agent as in claim 1, wherein each dose of said therapeutic agent containing from about 5 mg to about 200 milligrams of said first mucolytic.

10. The therapeutic agent as in claim 1, wherein said first mucolytic is 2-Mercaptoethane Sulfonate.

11. The therapeutic agent as in claim 1, wherein said second mucolytic is 2-Mercaptoethane Sulfonate.

12. The therapeutic agent as in claim 1, wherein the therapeutic agent is provided in a dry-powder inhaler suitable for self-administration.

13. The therapeutic agent as in claim 1, wherein the anti-infective agent further comprises a quinolone.

* * * * *